United States Patent
Honda et al.

(10) Patent No.: US 7,708,807 B2
(45) Date of Patent: May 4, 2010

(54) DEVICE FOR RECOVERING MATERIAL TO BE MEASURED AND METHOD FOR RECOVERING MATERIAL TO BE MEASURED

(75) Inventors: Katsuhisa Honda, Matsuyama (JP); Noriaki Hamada, Matsuyama (JP); Jun Kishino, Kyoto (JP); Kazuyuki Sawadaishi, Kyoto (JP)

(73) Assignees: Miura Co., Ltd., Matsuyama-shi (JP); Kyoto Electronics Manufacturing Co., Ltd., Kyoto-shi (JP)

( * ) Notice: Subject to any disclaimer, the term of this patent is extended or adjusted under 35 U.S.C. 154(b) by 988 days.

(21) Appl. No.: 10/583,729

(22) PCT Filed: Dec. 21, 2004

(86) PCT No.: PCT/JP2004/019080

§ 371 (c)(1),
(2), (4) Date: Jun. 20, 2006

(87) PCT Pub. No.: WO2005/062016

PCT Pub. Date: Jul. 7, 2005

(65) Prior Publication Data

US 2007/0138099 A1    Jun. 21, 2007

(30) Foreign Application Priority Data

Dec. 24, 2003   (JP)   ............... 2003-427465

(51) Int. Cl.
*B01D 53/00* (2006.01)
(52) U.S. Cl. .............. 95/149; 96/413; 73/863.61; 73/863.21; 73/863.23; 73/61.55; 73/866

(58) Field of Classification Search .............. 96/413; 73/868, 61.55, 863.21, 863.23, 863.61, 866; 210/656; 95/149
See application file for complete search history.

(56) References Cited

U.S. PATENT DOCUMENTS 3,020,128 A * 2/1962 Adcock et al. ............ 75/395

FOREIGN PATENT DOCUMENTS

| JP | 8-101102 A | | 4/1996 |
|---|---|---|---|
| JP | 08-101102 A | * | 4/1996 |
| JP | 2001-083052 A | | 3/2001 |
| JP | 2001-242150 A | | 9/2001 |
| JP | 2003-344378 A | * | 12/2003 |
| JP | 2003-344378 A | | 12/2003 |

* cited by examiner

*Primary Examiner*—Duane Smith
*Assistant Examiner*—Ives Wu
(74) *Attorney, Agent, or Firm*—Birch, Stewart, Kolasch & Birch, LLP

(57) ABSTRACT

Device for recovering a material to be measured comprising a reservoir filled with a sample holding material impregnated with a sample liquid in which a material to be measured is dissolved and an adsorbing column for adsorbing the material to be measured, wherein the reservoir and the adsorbing column are communicated by a straight pipe, and further communicated with a recovery vessel via a recovery pipe branched out the straight pipe. Accordingly, operations of opening/closing or switching a first valve provided on the in-flow side of the reservoir, a second valve provided on the out-flow side of the adsorbing column, and a third valve provided to a vent hole to the atmosphere in the recovery vessel, make it possible to recover the material to be measured without depositing the material on the valves.

12 Claims, 18 Drawing Sheets

| | RECOVERY PERCENTAGE (%) |
|---|---|
| 2378-TeCDD | 93 |
| 12378-PeCDD | 100 |
| 123478-HxCDD | 100 |
| 123678-HxCDD | 96 |
| 123789-HxCDD | 110 |
| 1234678-HpCDD | 105 |
| OCDD | 102 |
| 2378-TeCDF | 91 |
| 12378-PeCDF | 101 |
| 23478-PeCDF | 91 |
| 123478-HxCDF | 106 |
| 123678-HxCDF | 97 |
| 123789-HxCDF | 83 |
| 234678-HxCDF | 92 |
| 1234678-HpCDF | 104 |
| 1234789-HpCDF | 107 |

FIG. 9

| | LEVEL & TEQ RECOVERED BY DEVICE IN FIG. 16 | | LEVEL & TEQ RECOVERED BY THE INVENTION | |
|---|---|---|---|---|
| | LEVEL (ng/ml) | ng-TEQ/ml | LEVEL (ng/ml) | ng-TEQ/ml |
| 2378-TeCDD | 0.57 | 0.57 | 0.53 | 0.53 |
| 12378-PeCDD | 3.4 | 3.4 | 3.4 | 3.4 |
| 123478-HxCDD | 5.6 | 0.56 | 5.6 | 0.56 |
| 123678-HxCDD | 10 | 1 | 9.6 | 0.96 |
| 123789-HxCDD | 10 | 1 | 11 | 1.1 |
| 1234678-HpCDD | 61 | 0.61 | 64 | 0.64 |
| OCDD | 96 | 0.0096 | 98 | 0.0098 |
| 2378-TeCDF | 2.3 | 0.23 | 2.1 | 0.21 |
| 12378-PeCDF | 2.6 | 0.129 | 2.7 | 0.13 |
| 23478-PeCDF | 6.4 | 3.2 | 5.8 | 2.9 |
| 123478-HxCDF | 5.1 | 0.51 | 5.4 | 0.54 |
| 123678-HxCDF | 6.9 | 0.69 | 6.7 | 0.67 |
| 123789-HxCDF | 2.4 | 0.24 | 2 | 0.2 |
| 234678-HxCDF | 12 | 1.2 | 11 | 1.1 |
| 1234678-HpCDF | 27 | 0.27 | 28 | 0.28 |
| 1234789-HpCDF | 4.2 | 0.042 | 4.5 | 0.045 |
| OCDF | 16 | 0.0016 | 16 | 0.0016 |
| Total TEQ | | 13.7 | | 13.3 |

FIG. 10

| DEVICE SHOWN IN FIG.16 | DEVICE OF PRESENT APPLICATION |
|---|---|
| 12 | 5.7 |
| 12 | 2.7 |
| 14 | 0 |
| 13 | 1.1 |
| 17 | 4.6 |
| 4.9 | 1.2 |
| 1.8 | 0.1 |
| 15 | 0.1 |
| 13 | 2.4 |
| 13 | 5.8 |
| 15 | 3 |
| 15 | 1.6 |
| 19 | 1.1 |
| 13 | 1.1 |
| 6.1 | 0.2 |
| 6.7 | 0.2 |
| 0 | 0 |

FIG. 11

| | RECOVERY PERCENTAGE (%) |
|---|---|
| 2378-TeCDD | 93 |
| 12378-PeCDD | 100 |
| 123478-HxCDD | 100 |
| 123678-HxCDD | 96 |
| 123789-HxCDD | 110 |
| 1234678-HpCDD | 105 |
| OCDD | 102 |
| 2378-TeCDF | 91 |
| 12378-PeCDF | 101 |
| 23478-PeCDF | 91 |
| 123478-HxCDF | 106 |
| 123678-HxCDF | 97 |
| 123789-HxCDF | 83 |
| 234678-HxCDF | 92 |
| 1234678-HpCDF | 104 |
| 1234789-HpCDF | 107 |

DEVICE FOR RECOVERING MATERIAL TO BE MEASURED AND METHOD FOR RECOVERING MATERIAL TO BE MEASURED

TECHNICAL FIELD

The invention relates to a device for recovering a material to be measured included in a sample liquid, and a method for recovering the material to be measured.

BACKGROUND ART

Hazardous materials such as dioxin are included in exhaust gases generated by incinerating facilities, metal smelting facilities, and the like. Recently, it is urged to establish a simple and precise method for measuring an amount of dioxin included in the exhaust gas.

As a method for measuring the amount of dioxin included in the exhaust gas, it is possible to utilize 'JIS K 0311' regulated by Japanese Industrial Standards. In the method provided by 'JIS K 0311', both a solvent to dissolve the dioxin together with various materials included in the exhaust gas and an absorbing material to adsorb the dioxin together with the various materials are used to collect the dioxin, whereby the dioxin is extracted together with the other materials included in the exhausted gas. Therefore, in order to measure the amount of dioxin, it is necessary for recovering only the dioxin from the other dissolved material contained in the exhaust gas.

FIG. 16 shows a conventional recovery device.

The device includes a reservoir 601, and an adsorbing column 603 being communicated with a bottom of the reservoir 601. A filter material S2, such as silica gel, for collecting the materials contained in the solvent except the dioxin, and a sample holding material S1 for impregnating a solution thereto, the solution in which the materials included in the exhaust gas are dissolved, are packed sequentially into the reservoir 601 from the bottom thereof. The adsorbing column 603 is filled with an adsorbing material S3 for adsorbing the dioxin only, like activated carbon, alumina, etc.

In case of recovering the dioxin by using the device, a user impregnates the sample holding material S1 of the reservoir 601 with a specific volume of the sample liquid extracted as above, then, runs the solvent (hexane, in this case) therein from the top of the reservoir 601. The solvent elutes some materials including the dioxin through the filter material S2, and then runs down the adsorbing column 603. Since the adsorbing column 603 is filled with the adsorbing material S3, the adsorbing material S3 adsorbs the dioxin only, and the solvent is discharged from the bottom of the adsorbing column 603 to the outside.

After the solvent is drained out, as shown in FIG. 17, the user removes the adsorbing column 603 from the reservoir 601, turns the adsorbing column 603 upside down, and runs an eluant for dioxin therein from the top. The eluant is received by a recovery vessel 607. The eluant ran into the adsorbing column 603 is drained from the bottom of the adsorbing column 603 while dissolving the dioxin adsorbed on the adsorbing material S3.

The drained eluant is recovered by the recovery vessel as mentioned above, whereby it is possible to recover the eluant in which only the dioxin is dissolved.

Additionally, there is provided another device for recovering the material to be measured, by which the user can recover the eluant containing the dioxin only without the operations that the user turns the adsorbing column upside down and runs the solvent. The device is configured as shown in FIG. 18; the reservoir 601 and the adsorbing column 603 shown in FIG. 16 are connected by a tube 602 via two ports of a 3-way valve 606, and the other port of the 3-way valve is connected to a recovery pipe 605. Opening and closing the 3-way valve is controlled by a control unit as follows.

At pushing a start key of the device, the control unit controls the 3-way valve to communicate the reservoir 601 and the adsorbing column 603. Then the control unit runs the solvent into the reservoir 601 from the top. The injected solvent elutes plural kinds of materials containing the dioxin from the reservoir 601 through the filter material S2, like the solvent injected into the device shown in FIG. 16. When the solvent runs through the adsorbing column 603, the solvent allows the adsorbing material S3 filled in the adsorbing column 603 to adsorb the dioxin, and then drained out.

The control unit switches the 3-way valve 606 to communicate the adsorbing column 603 and the recovery pipe 605, and runs the eluant into the adsorbing column 603 from the bottom. The eluant elutes the dioxin collected by the adsorbing column 603, and runs into the recovery vessel 607 provided at an end of the recovery pipe 605 through the tube 602 to the recovery pipe 605.

Accordingly, the user can recover the eluant, in which only the dioxin is dissolved, by pushing the start key only.

However, in the dioxin recovery process made by the device shown in FIG. 18, when the solvent and the eluant in which dioxin is dissolved run through the 3-way valve 606, the dioxin is attached to the 3-way valve 606, and the 3-way valve 606 is contaminated with the dioxin. Therefore, whenever the recovery process is performed, the 3-way valve 606 needs to be cleaned.

The dioxin is adhered to and remains at the 3-way valve 606, with the result that this reduces the recovery percentage of the dioxin impregnated to the sample holding material S1. The contamination caused by the insufficient cleaning will reflect a bad influence on the next measurement.

Therefore, the present invention has an object to provide a device for recovering a material to be measured, wherein the material to be measured, such as the dioxin, can be recovered at high recovery percentage, and the cleaning of the valve is not required.

DISCLOSURE OF INVENTION

The present invention is based on a device for recovering a material to be measured in a recovery vessel, by dissolving the material held by a reservoir in a solvent, impregnating the solvent to an adsorbing column, and eluting the adsorbed material with an eluant.

The device is configured so that an out-flow side of the reservoir is communicated with the adsorbing column by a straight pipe having a branch node at a middle of the straight pipe, and a recovery pipe communicated with the recovery vessel is connectable to the branch node.

Moreover, it is configured so that a first valve on the in-flow side of the reservoir opens and closes a path to feed the solvent therein, a second valve on an out-flow side of the adsorbing column switches between a discharge of the solvent and a supply of an eluant for recovering the material adsorbed in the adsorbing column, the recovery vessel is connected to the recovery pipe, and a vent hole opens the recovery vessel to outside via a third valve.

Under such configuration, when each valve is operated for the solvent supply process and the recovery process respectively, the material to be measured can be recovered without adhering the solvent and the eluant to the valves.

That is to say, a solvent supply control unit opens the first valve, turns the second valve to discharge the solvent, and closes the vent hole by the third valve, at feeding the solvent in the reservoir. A recovery control unit closes the first valve, turns the second valve to supply the eluant, and opens the vent hole by the third valve, at eluting the material to be measured adsorbed in the adsorbing column.

When it is configured that the second valve is a 3 and more way valve, an end on a side of the adsorbing column is connectable to another end selectively, if the eluant may be fed in the adsorbing column so as to correspond to plural kinds of materials to be measured adsorbed in the adsorbing column, it is possible to recover an object material to be measured.

To correspond to a plurality of eluants, the invention may have the plural branch nodes.

In addition to the solvent supply control unit and the recovery control unit, the device may include a drying control unit. The device has a gas vessel filled with a gas for drying the adsorbing column, and a gas supply pipe for feeding the gas in the adsorbing column. The drying control unit communicates the gas supply pipe with the recovery vessel by operating the third valve, and feeds the gas for drying in the adsorbing column, and then dries the adsorbing column and the recovery pipe after supplying the solvent.

BRIEF DESCRIPTION OF THE DRAWINGS

FIG. 9 shows a diagram indicating a level of material to be measured that is recovered by the conventional device and the device of the present invention.

FIG. 10 shows a diagram indicating a coefficient of variation about the recovery percentage at the recovery process performed by the device of the present invention and the conventional device.

FIG. 11 shows a diagram indicating the recovery percentage when the recovery process is performed by the device of the present invention.

BEST MODE FOR CARRYING OUT THE INVENTION

Embodiment 1

Figure 1:
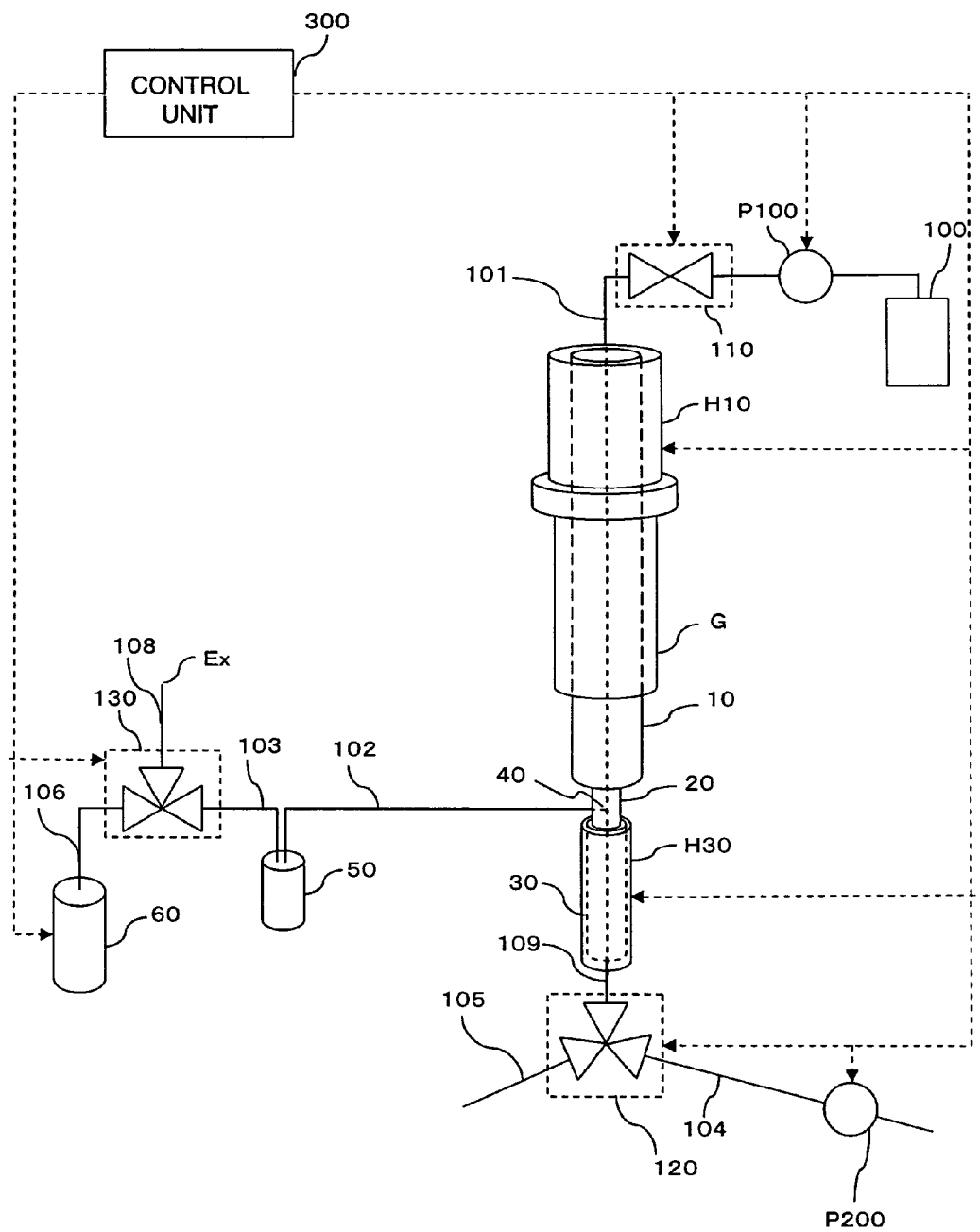
FIG. 1 shows an outline view of a device for recovering material to be measured in the present invention.
Figure 2:
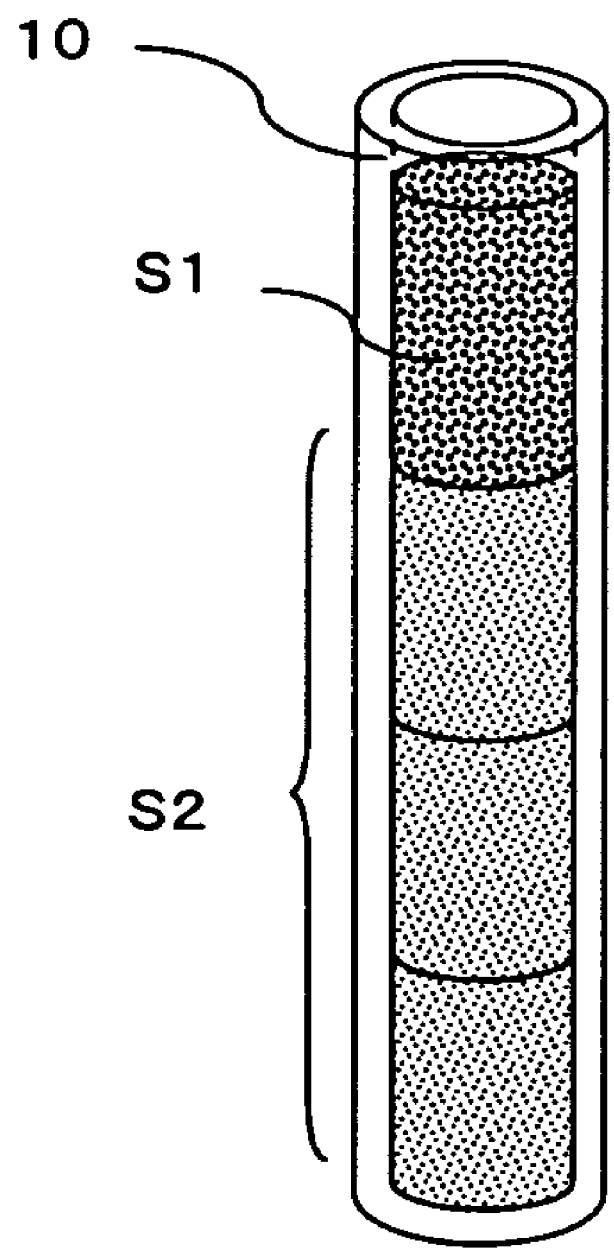
FIG. 2 shows an outline view of details of a reservoir.

FIG. 1 shows an outline view of a device for recovering material to be measured in the present invention. The device of the present invention is provided with a glass reservoir 10. The reservoir 10 has a lower part that is filled with a filter material S2 made of a plurality of silica layers, and an upper part that is filled with a sample holding material S1, as shown in FIG. 2. An exterior of the reservoir 10, of which an upper part is covered by a heater H10 so as to correspond to the sample holding material S1, and the lower part is covered by a heater jacket G so as to conduct heat of the heater to the filter material S2.

A top end of the reservoir 10 is communicated with an end of a solvent supply pipe 101. The solvent supply pipe 101 is connected to a solvent vessel 100 through a 2-way valve (a first valve) 110 and a pump P100. A bottom end of the reservoir 10 is communicated with a top of a glass adsorbing column 30 via a straight pipe 20.

An exterior of the adsorbing column 30 is covered by a heater H30, meanwhile an interior of the adsorbing column 30 is filled with an adsorbing material S3 to adsorb the material to be measured, such as alumina, activated carbon, and so on.

A bottom of the adsorbing column 30 is communicated with an end of a common pipe 109. Another end of the common pipe 109 is connected to an eluant supply pipe 104 and a solvent discharge pipe 105 via a 3-way valve 120 (a second valve). By switching the 3-way valve 120, one of the two pipes 104 and 105 is communicated with the adsorbing column 30 through the common pipe 109.

The straight pipe 20 has a branch node 40, and communicated with a recovery pipe 102 via the branch node 40. Another end of the recovery pipe 102 is communicated with a recovery vessel 50.

The recovery vessel 50 is communicated with an end of a discharge pipe 103, and another end of the discharge pipe 103 is connected to a gas supply pipe 106 and a vent pipe 108 via a 3-way valve (a third valve) 130. The gas supply pipe 106 is communicated with a gas vessel 60 filled with nitrogen gas, as well as the vent pipe 108 is communicated with a vent hole Ex. When the 3-way valve 130 is switched, the discharge pipe 103 is blocked off from the pipes 106 and 108 or communicated with one of the pipes 106 and 108. When the discharge pipe 103 is communicated with the vent pipe 108, the recovery vessel 50 is communicated with the vent hole Ex, and the recovery vessel 50 is opened to outside.

Figure 3:
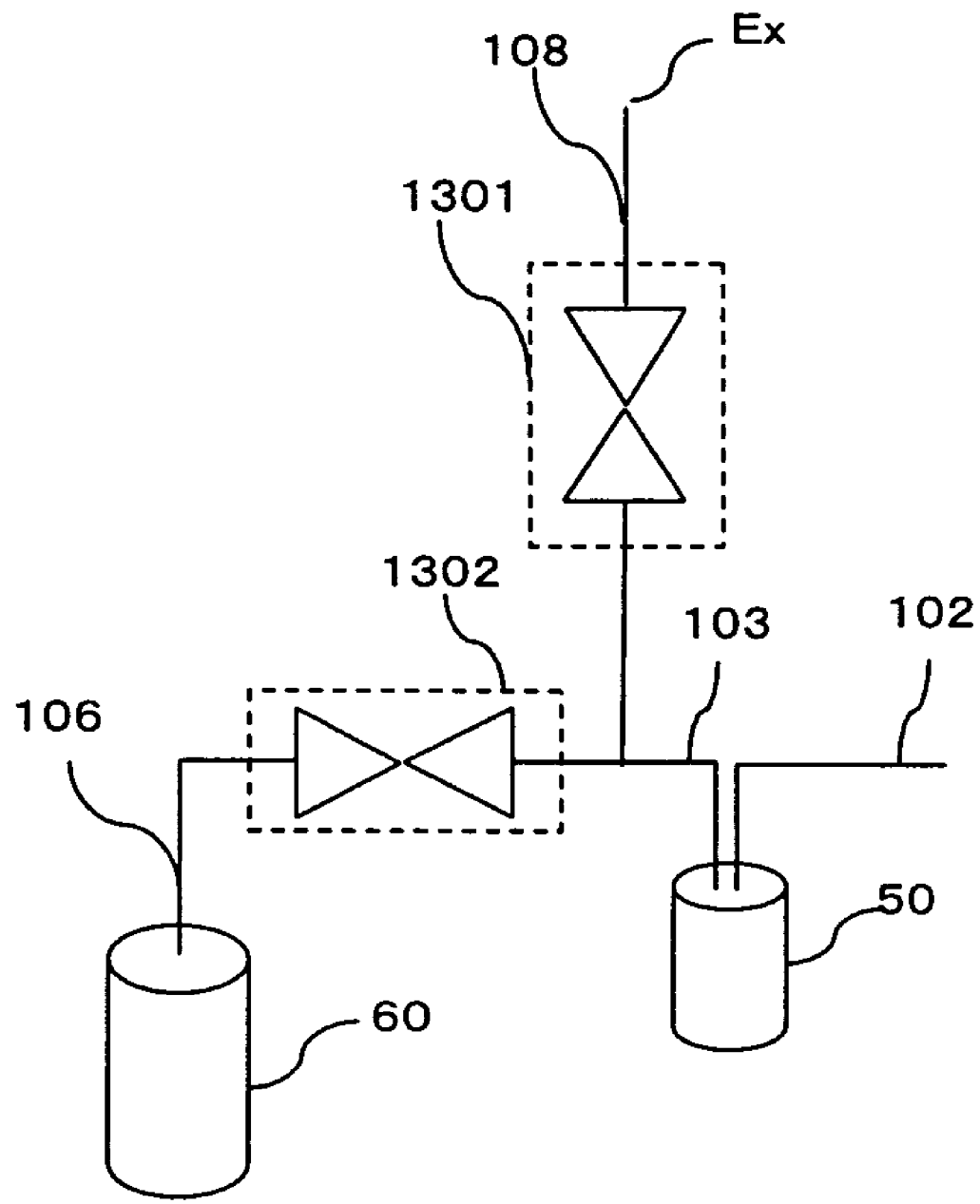
FIG. 3 shows a diagram illustrating a structure wherein a discharge pipe, a gas supply pipe, and a vent pipe are connected by two valves.

In FIG. 1, the discharge pipe 103, the gas supply pipe 106, and the vent pipe 108 are connected by the 3-way valve, but those may be connected by different two valves 1301 and 1302, as shown in FIG. 3.

When the device need not to include the gas supply pipe 106 and the gas vessel 60 as described later, a 2-way valve may be used as the third valve instead of the 3-way valve 130.

Figure 4:
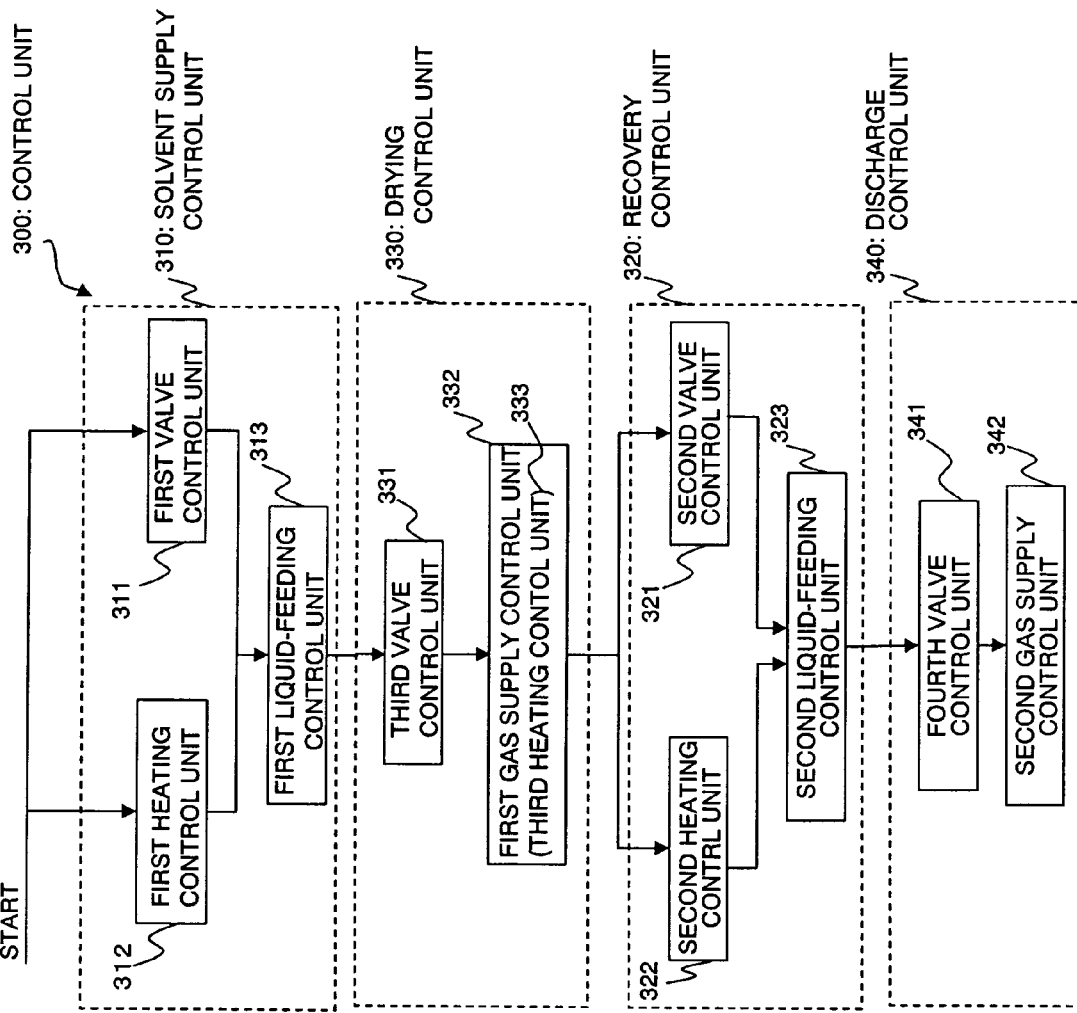
FIG. 4 shows a functional block diagram of a control unit.

The device of the present invention is provided with a control unit 300 shown in FIG. 4. The control unit 300 controls the three valves 110, 120, 130 and the heater.

Here is the process of recovering the dioxin included in the exhaust gas generated from the waste incinerating facilities and the metal smelting facilities that is performed by means of the above-mentioned device.

According to the method regulated by 'JIS K 0311', the user collects exhaust gas components from the exhaust gas by means of solvent and adsorbent. Specifically, the user feeds the exhaust gas in the solvent, such as water and diethylene glycol, to dissolve the exhaust gas components therein, as well as collects the exhaust gas components using divinylbenzen resin as the adsorbent. Then the user performs a liquid-liquid extraction and elution for the solvent in which the gas components are dissolved, and performs a Soxhlet extraction for the adsorbent, to generate raw extracted solution in which the materials included in the exhaust gas are dissolved, such as a specific volume of toluene. The user dispenses the generated specific volume of the raw extracted solution to an eggplant-shaped flask, and evaporates and condenses the dispensed raw extracted solution by evaporator. The user adds a specific volume of hexane to the condensed raw extracted solution to generate a sample liquid.

Figure 5:
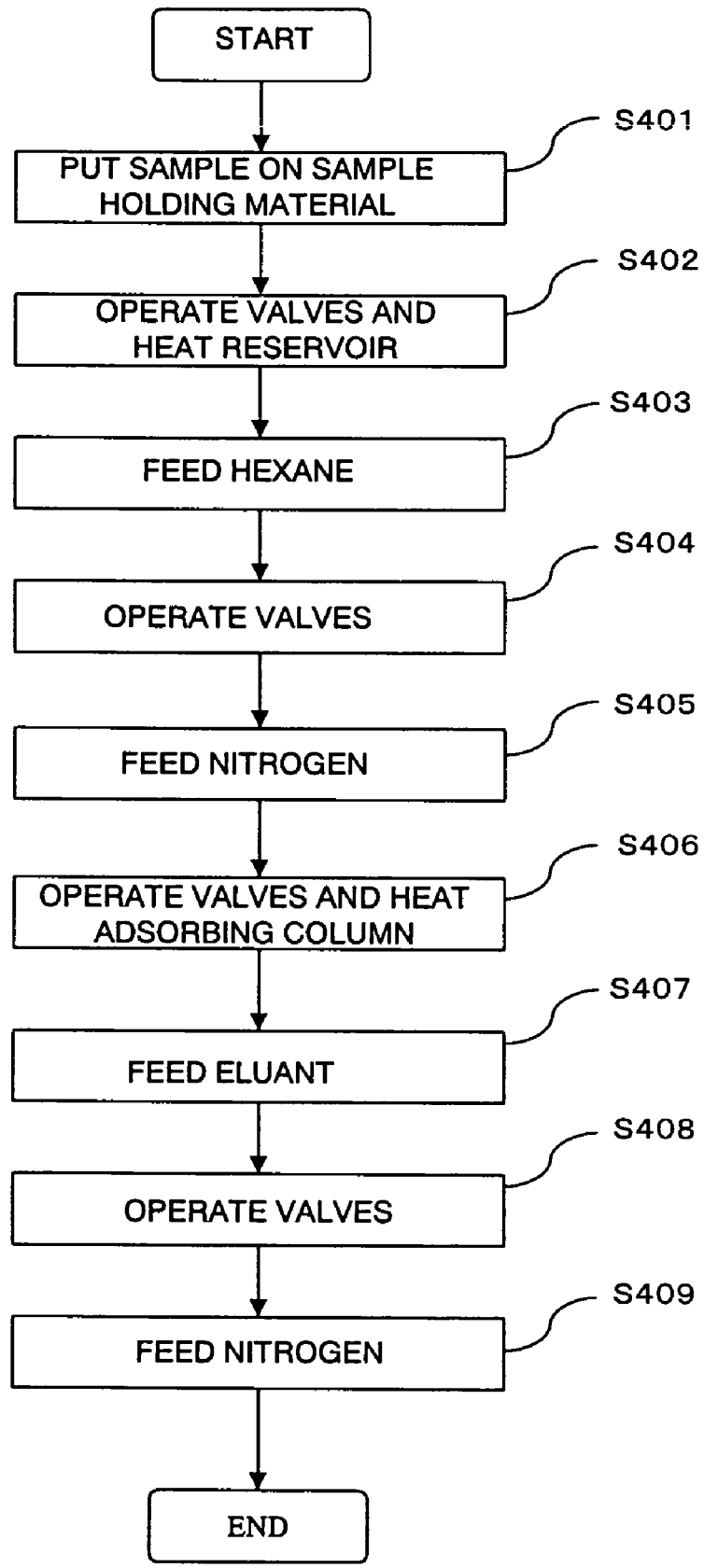
FIG. 5 shows a flowchart illustrating a process of recovering material to be measured.

After generating the sample liquid, the user impregnates a sample holding material filled in the reservoir 10 with a specific volume of the generated sample liquid (FIG. 5, S401).

After that, the user pushes a start key (not shown in the figure) provided to a keyboard for operating the control unit 300. At pushing the start key, a solvent supply control unit 310 (a first valve control unit 311, a first heating control unit 312, and a first liquid-feeding control unit 313) is activated and feeds the solvent (hexane, in this embodiment) as follows.

Figure 6:
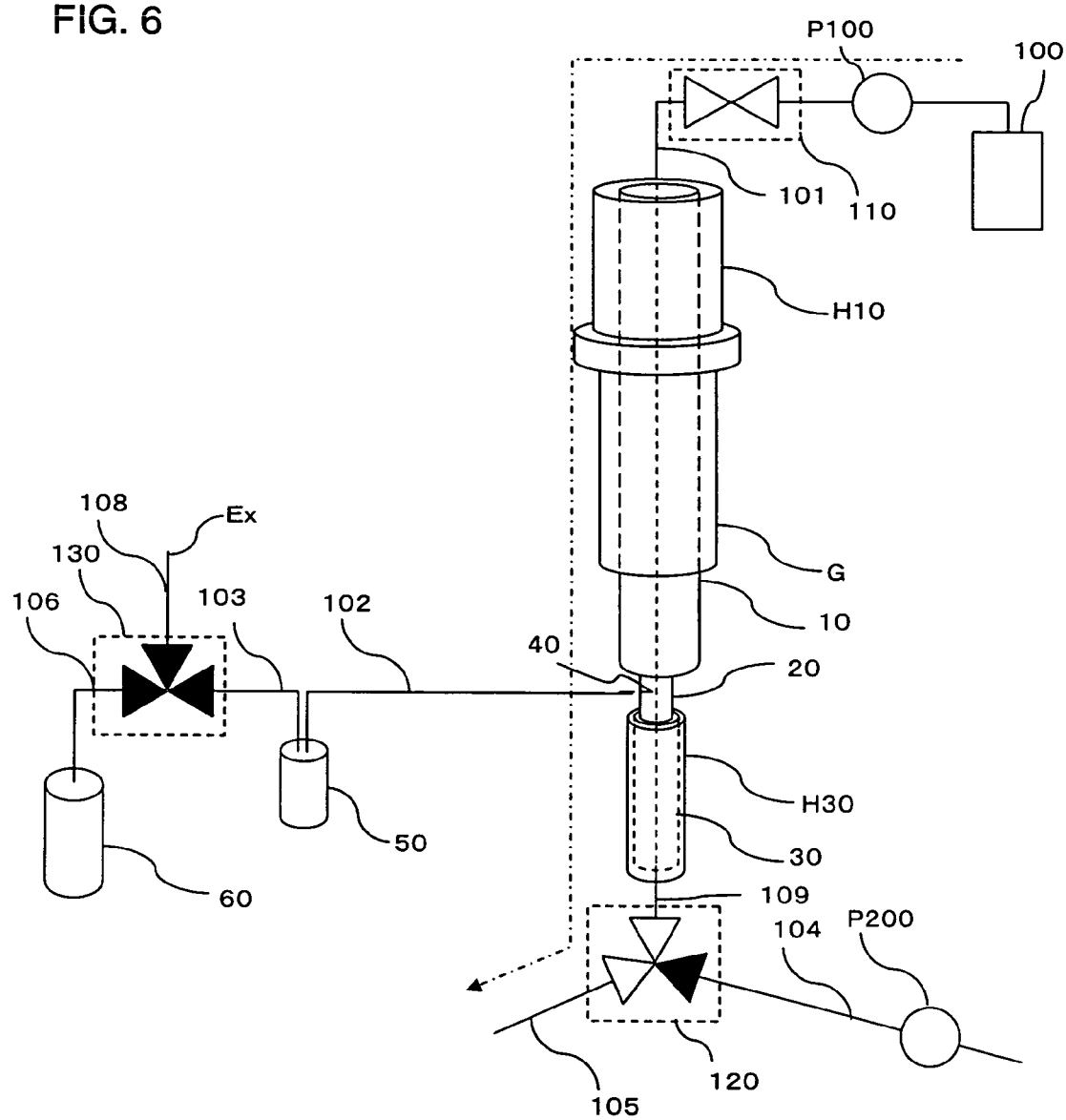
FIG. 6 shows a state of a valve in an adsorbing process.

Specifically, pushing the start key is notified to the first valve control unit 311 and the first heating control unit 312 shown in FIG. 4. Upon receipt of the notice, the first valve control unit 311 opens the 2-way valve 110, communicates the common pipe 109 with the solvent discharge pipe 105 via the 3-way valve 120, and blocks the discharge pipe 103 from the gas supply pipe 106 and the vent pipe 108 by the 3-way valve 130. In FIG. 6 and after-mentioned FIGS. 7 and 8, where each end of pipes 101 to 109 is communicated with any end of other pipes 101 to 109, the end is illustrated by a white triangle, and where blocked off from any of other pipes, each end of pipes 101 to 109 is illustrated by a black triangle.

The first valve control unit 311 operates the valves 110, 120, and 130, which is notified to the first liquid-feeding control unit 313.

On the other hand, at being notified that the start key is pushed, the first heating control unit 312 heats the reservoir 10 by the heater H10. When the temperature becomes 60° C., the first heating control unit 312 notifies it to the first liquid-feeding control unit 313, and keeps the temperature of the reservoir 10 at 60° C. (FIG. 5, S402).

In response to the notices from the first valve control unit 311 and the first heating control unit 312, the first liquid-feeding control unit 313 drives the pump P100 to feed the specific volume V1 of solvent from the solvent supply pipe 101 to the reservoir 10 at a specific rate V2 (feeding 60 ml of hexane at 2.5 ml per minute, for example) (FIG. 5, S403). The specific volume V1 and the specific rate V2 are determined based on the relation of an inner diameter of the reservoir 10, a volume of the sample holding material S1, and a volume of the filter material S2.

When the solvent fed to the reservoir 10 runs through the sample holding material S1, the solvent is preparatively purified by the filter material S2 while eluting the dioxin and the other materials impregnated in the sample holding material S1, and then runs out from the bottom of the reservoir 10 to the straight pipe 20. According to the preliminary purification, specific materials dissolved in the solvent, except the dioxin, can be collected by the filter material S2.

At feeding the solvent into the reservoir, since the 3-way valve 130 blocks the discharge pipe 103 from the gas supply pipe 106 and the vent pipe 108 as shown in FIG. 6, there is no possibility that the solvent runs into the recovery pipe 102 from the straight pipe 20. Therefore, after the solvent passed through the reservoir 10, it runs down to the solvent discharge pipe 105 through the adsorbing column 30. The adsorbing column 30 was filled with the adsorbing material S3 for adsorbing the dioxin only. The dioxin is adsorbed to the adsorbing material S3 when the solvent runs through the adsorbing column 30.

After the feeding of the solvent, a drying control unit 330 (a third valve control unit 331, a first gas supply control unit 332, and a third heating control unit 333) is activated, and dries the adsorbing column as follows.

Figure 7:
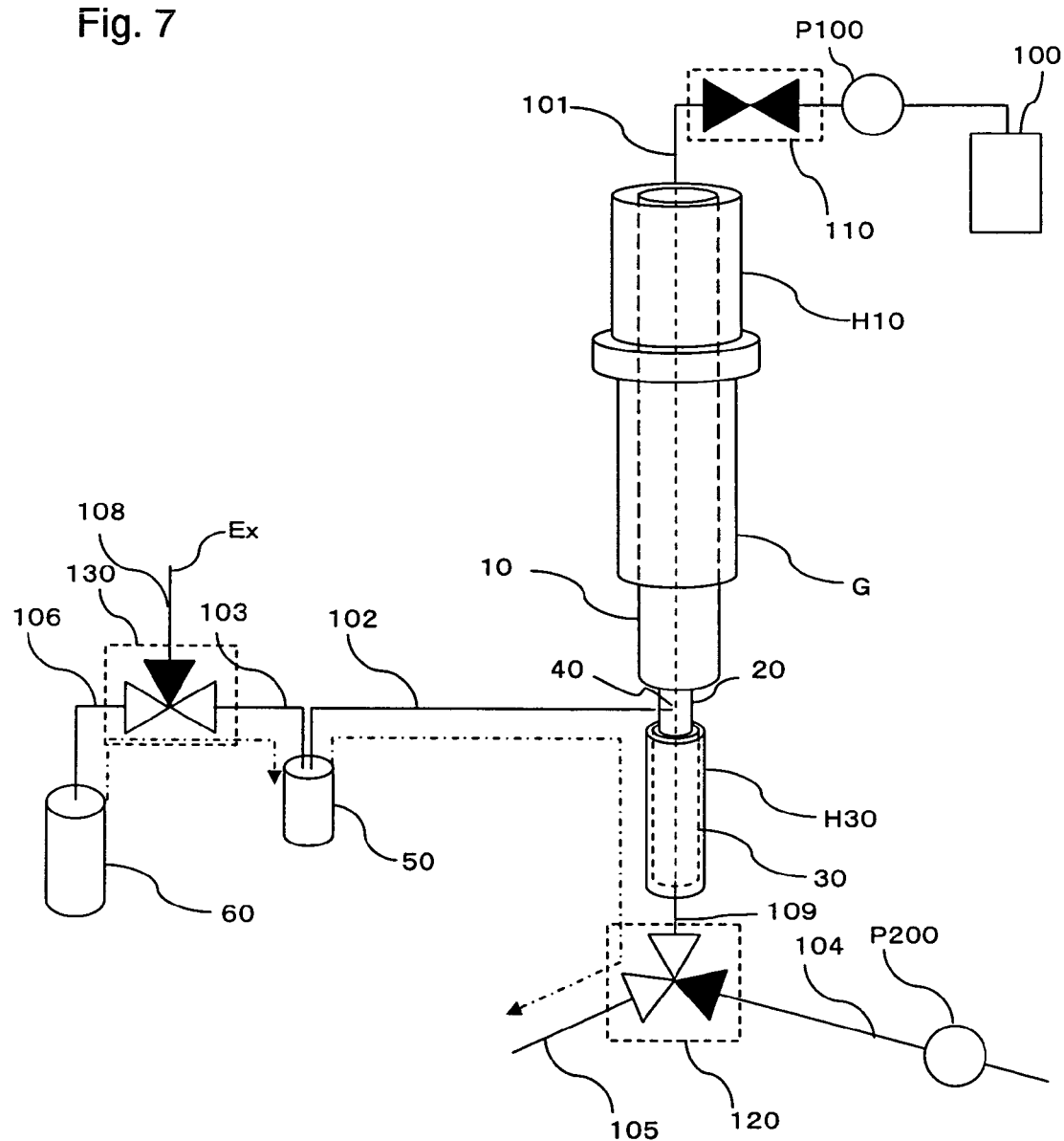
FIG. 7 shows a state of valves in a drying process and a discharging process.

That is to say, when the feeding of the solvent is terminated, the first liquid-feeding control unit 313 notifies the third valve control unit 331 of the termination. In response to the notice, the third valve control unit 331 closes the 2-way valve 110, and communicates the discharge pipe 103 with the gas supply pipe 106 by the 3-way valve 130 without operating the 3-way valve 120, as shown in FIG. 7 (FIG. 5, S404). The third valve control unit 331 operates the valves 110, 120, and 130, and notifies it to the first gas supply control unit 332. The first gas supply control unit 332 feeds the nitrogen filled in the gas vessel 60 into the gas supply pipe 106 by means of a compressor or the like (FIG. 5, S405).

When the nitrogen is fed out, the 2-way valve 110 is closed as shown in FIG. 7. The nitrogen goes through the discharge pipe 103, the recovery vessel 50, the recovery pipe 102, the straight pipe 20, the adsorbing column 30, and the common pipe 109, and then flows in the solvent discharge pipe 105. This dries the adsorbing column 30. However, in this embodiment, it is possible to use the third heating control unit 333 in addition to the nitrogen gas. That is to say, the third heating control unit 333 heats the heater H30 to raise the temperature of the adsorbing column 30, and then feeds the nitrogen gas therein, whereby the drying can be expedited.

After the first gas supply control unit 332 feeds the nitrogen in the adsorbing column 30 for a time enough to dry the adsorbing material S3 thereof, it notifies a second valve control unit 321 and a second heating control unit 322 that the adsorbing column 30 was dried.

Subsequently, a recovery control unit 320 (the second valve control unit 321, the second heating control unit 322, and a second liquid-feeding control unit 323) is activated, and recovers the material to be measured as follows.

Figure 8:
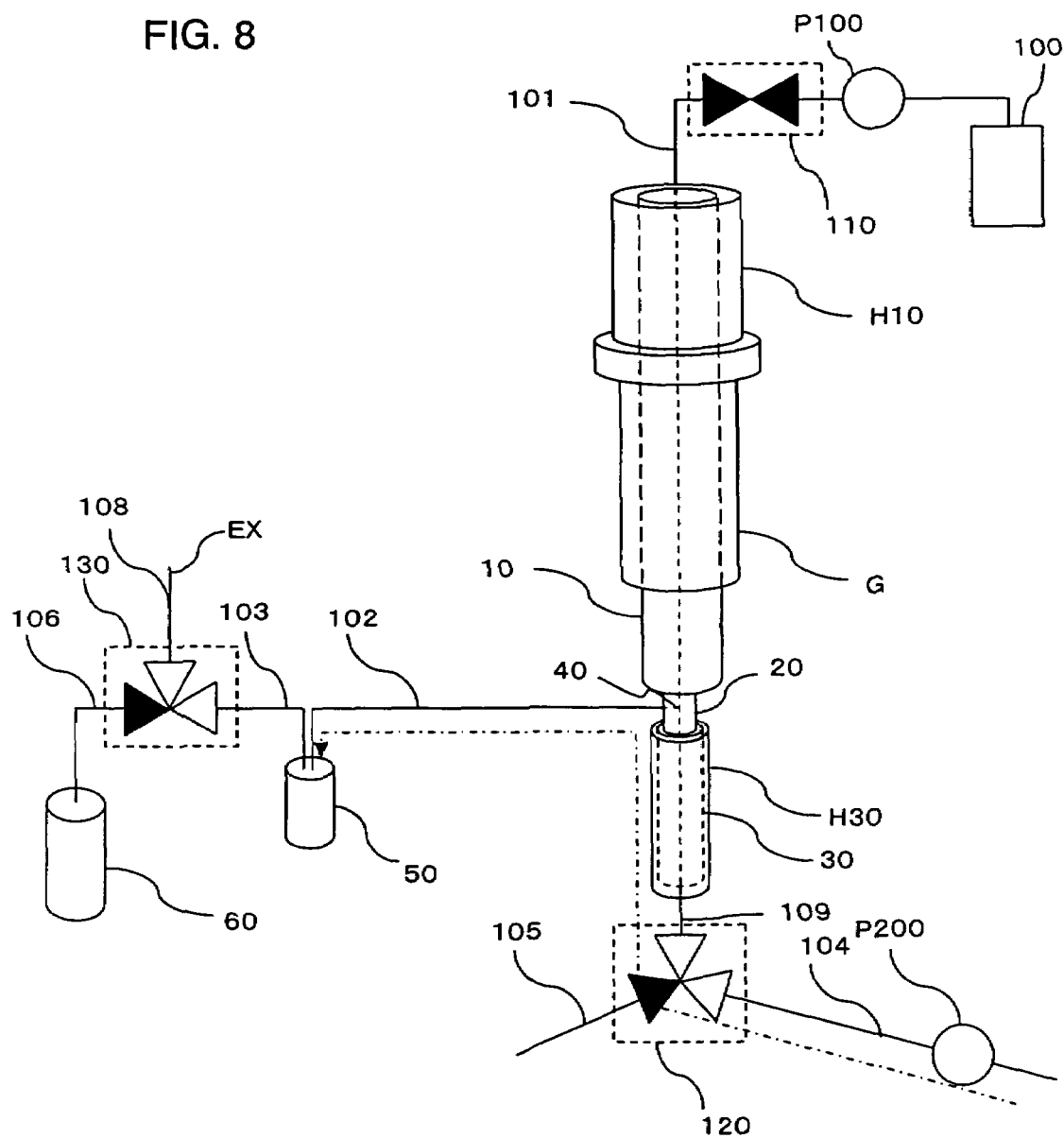
FIG. 8 shows a state of valves when a material to be measured is recovered.

At receiving the notice that the adsorbing column 30 was dried, the second valve control unit 321 keeps closing the 2-way valve 110, communicates the common pipe 109 with the eluant supply pipe 104 through the 3-way valve 120, and communicates the discharge pipe 103 with the vent pipe 108 through the 3-way valve 130, as shown in FIG. 8. The second valve control unit 321 operates the valves 110, 120, and 130, and then notifies the second liquid-feeding control unit 323 of the operation.

On the other hand, upon receipt of the notice that the adsorbing column 30 was dried, the second heating control unit 322 heats the adsorbing column 30 by means of the heater H30. When the temperature becomes 60° C., the second heating control unit 322 notifies the second liquid-feeding control unit 323 of it, and keeps the temperature of the adsorbing column 30 at 60° C. (FIG. 5, S406). At receiving from the second valve control unit 321 that the valves were operated and receiving from the second heating control unit 322 that the temperature became 60° C., the second liquid-feeding control unit 323 feeds a specific volume V3 of the eluant (toluene, or dimethyl sulfoxide) from the eluant supply pipe 104 to the adsorbing column 30 at a specific rate V4 (2.5 ml at 1.25 ml per minute) (FIG. 5, S407). In the embodiment, the eluant supply pipe 104 is connected to the bottom of the adsorbing column 30, so that the second liquid-feeding control unit 323 pumps the eluant into the adsorbing column 30 by means of the pump P200. Besides the specific volume V3 and the specific rate V4 are determined based on the inner diameter of the adsorbing column 30 and the volume of the adsorbing material S3.

While feeding the eluant therein, the 2-way valve 110 is closed, the discharge pipe 103 is communicated with the vent pipe 108, as shown in FIG. 8. Accordingly, the eluant runs through the common pipe 109, the adsorbing column 30, the straight pipe 20, and the recovery pipe 102, and then runs into the recovery vessel 50. Since the dioxin adsorbed to the adsorbing material S3 is eluted when the eluant runs through the adsorbing column 30, it is possible to recover in the recovery vessel 50 the eluant in which the dioxin is dissolved.

After the second liquid-feeding control unit 323 terminates the feeding of the specific volume of the eluant, the second liquid-feeding control unit 323 activates a discharge control unit 340 (a fourth valve control unit 341, and a second gas supply control unit 342), and drains the eluant staying in the adsorbing column 30 and the recovery pipe 102 as follows.

At terminating the feeding of the specific volume the eluant, the second liquid-feeding control unit 323 notifies the termination to the fourth valve control unit 341 and the second gas supply control unit 342.

When being notified the termination of the feeding of the eluant, the fourth valve control unit 341 turns the valves 110, 120, and 130 to the state as shown in FIG. 7 (FIG. 5, S408), and then notifies the second gas supply control unit 342 of the change. In response to the notice, the second gas supply control unit 342 feeds the nitrogen from the gas vessel 60 by means on a compressor or the like. At this time, the 2-way valve 110 is closed, the 3-way valve 120 communicates the common pipe 109 with the solvent discharge pipe 105, and the 3-way valve 130 communicates the gas supply pipe 106 with the discharge pipe 103, as shown in FIG. 7. Accordingly, the nitrogen goes through the discharge pipe 103, the recovery vessel 50, the recovery pipe 102, the straight pipe 20, the adsorbing column 30 and the common pipe 109, and then discharged to the solvent discharge pipe 105.

The valve change made by the fourth valve control unit 341 and the pumping of nitrogen made by the second gas supply control unit 342 are performed immediately after the specific volume V3 of the eluant (2.5 ml) was injected. Therefore, at starting the pumping of the nitrogen, some of the eluant running in the recovery pipe 102, the adsorbing column 30 and the common pipe 109 do not reach the recovery vessel 50. The direction that the nitrogen runs in the recovery pipe 102, the adsorbing column 30, and the common pipe 109 is opposite to the direction that the eluant runs in the recovery pipe 102, the adsorbing column 30, and the common pipe 109, so that all the eluant not reaching the recovery vessel 50 is discharged to the solvent discharge pipe 105 together with the nitrogen.

As described above, when the nitrogen is fed immediately after the specific volume (V3) of the eluant was fed, a recovered volume (V5) of the eluant in the recovery vessel 50 is less than the specific volume (V3). However, if it is possible to dissolve all the dioxin adsorbed to the adsorbing material S3 in the volume V5 of the eluant, all the dioxin can be collected only by recovering the volume (V5) of the eluant first. Accordingly, the residual volume (V3-V5) of the eluant may be discharged together with the nitrogen.

Therefore, the volume of the eluant recovered in the recovery vessel 50 when the feeding of the eluant has been terminated is a volume enough to dissolve all the dioxin adsorbed to the adsorbing material S3. The difference between the volume of the eluant fed from the eluant supply pipe 104 and the volume of the eluant recovered in the recovery vessel 50 is determined based on a length from the eluant supply pipe 104 to the common pipe 109, and the distance between the valve 120 and the recovery vessel 50. Therefore, the eluant volume to be flowed is desired to be determined based on those lengths and the distance.

Instead of the above-mentioned control method using the nitrogen, there is another method of controlling the volume of the eluant to be recovered in the recovery vessel 50. It may be configured that a sensor to measure the volume of the eluant recovered in the recovery vessel 50 is provided to the recovery vessel 50. When the sensor detects that the recovery vessel 50 recovered the volume of the eluant to be recovered, the fourth valve control unit 341 switches the valves 110, 120, and 130 without receiving the notice from the second liquid-feeding control unit 323, and then the second gas supply control unit 342 feeds the nitrogen.

In the present invention, the adsorbing column 30 is dried by the nitrogen before the eluant is injected therein, as described above. This drying process is indispensable only for a device that cannot measure the volume of the dioxin when the eluant recovered in the recovery vessel 50 includes the solvent (Hexane, in this embodiment). Therefore, if the device for measuring the dioxin can measure the dioxin even though the eluant includes the solvent, the above-mentioned drying process is not required. When the drying process is not required and the volume of the eluant recovered in the recovery vessel 50 can be controlled using the measuring sensor, the gas vessel 60 and the gas supply pipe 106 are not required, and in this case, a 2-way valve can be used to the valve 130.

Figure 16:
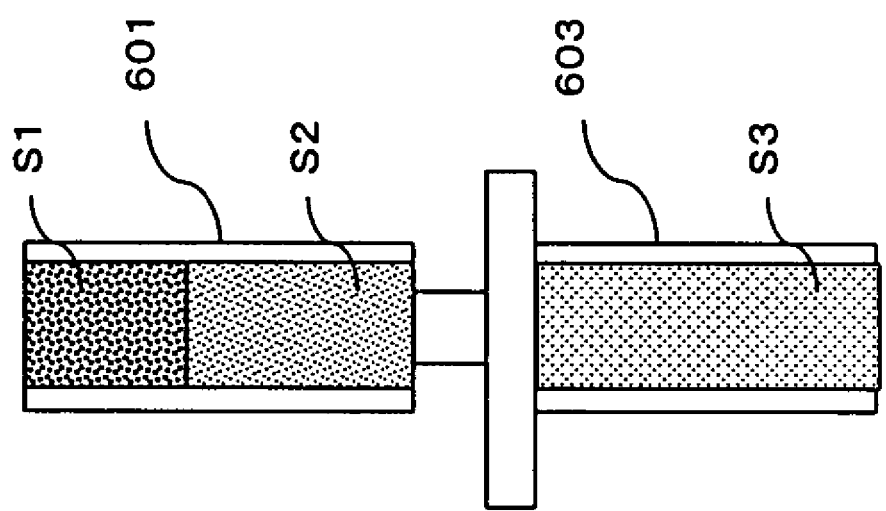
FIG. 16 shows a conceptual diagram illustrating a conventional device for recovering material to be measured.
Figure 17:
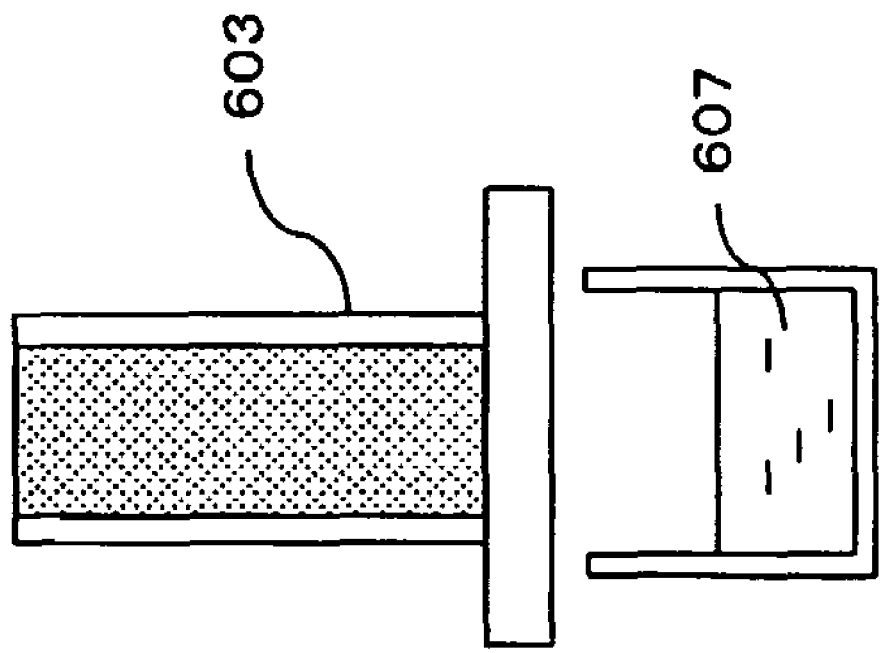
FIG. 17 shows a conceptual diagram illustrating a conventional device for recovering a material to be measured.
Figure 18:
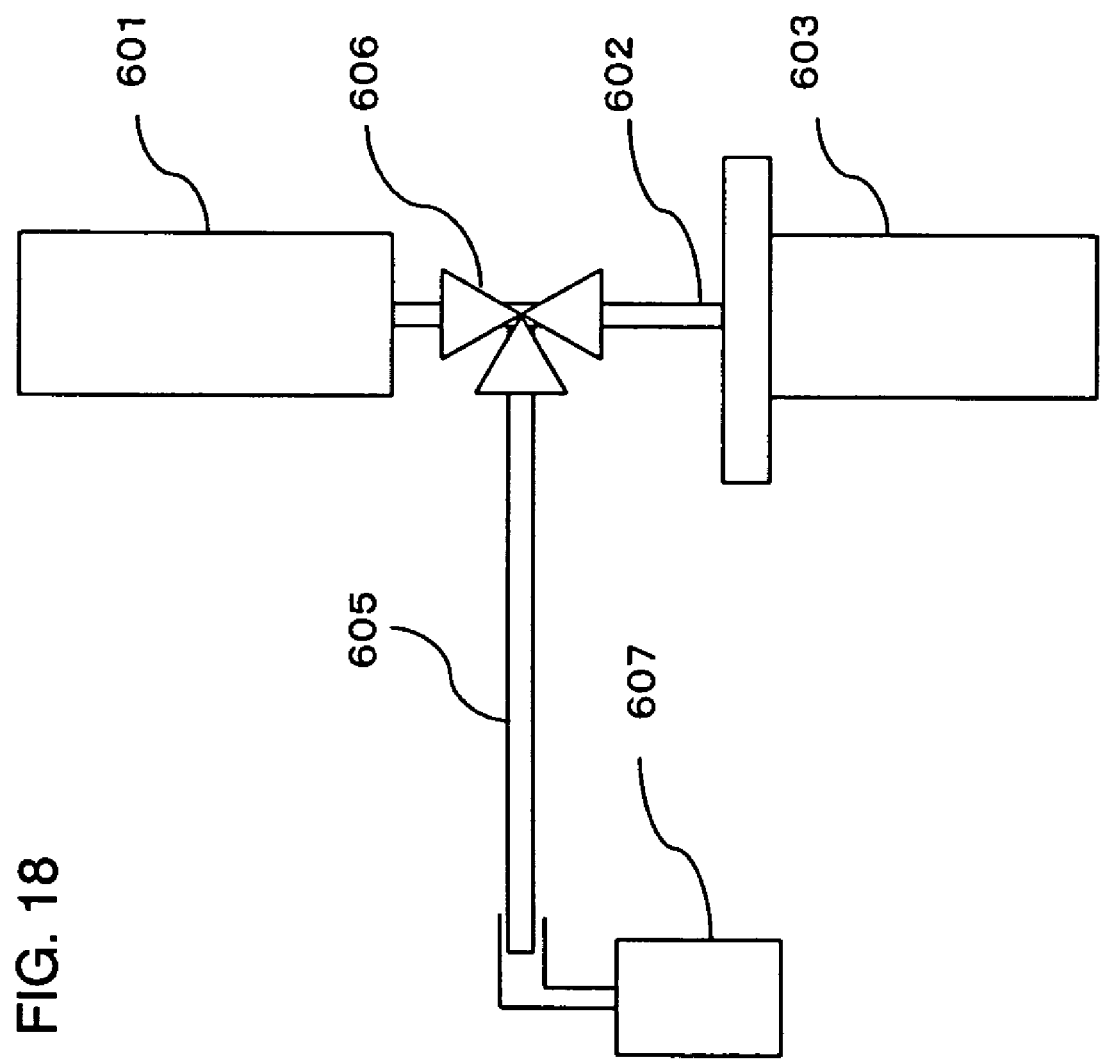
FIG. 18 shows a conceptual diagram illustrating a conventional device for recovering a material to be measured.

FIG. 9 shows a level and a TEQ (Toxic Equivalent Quantity) value of the dioxin recovered by the device of the present invention, and a level and a TEQ value of the dioxin recovered by the conventional device in FIG. 16. Besides, the TEQ value is the level of the dioxin multiplied by the toxic equivalency factor of the dioxin. In case of both devices, the sample liquid impregnated to the sample holding material S1 is the same volume, and the exhaust gas including the same compounds is sampled by the same method.

As shown in FIG. 9, it is apparent that the level and the TEQ value are the same in both the device of the present invention and the device in FIG. 16.

FIG. 10 shows a coefficient of variation of the volume of the recovered dioxin where respective the device of the present invention and the device in FIG. 16 performs the recovery process three times. The coefficients of variation where the device of the present invention performs the recovery process three times are smaller than the other. Therefore, it is possible to understand that the steady recovery process can be performed by the device of the present invention.

FIG. 11 shows the recovery percentage when the material to be measured is recovered by the device of the present invention. The recovery percentage is the amount of the dioxin recovered in the recovery vessel 50 that is divided by the amount of the dioxin included in the sample liquid impregnated to the sample holding material S1. As shown in FIG. 11, the recovery percentage of each material is very high.

Therefore, the device in the invention can perform a steadier recovery process than the conventional device.

Embodiment 2

Figure 14:
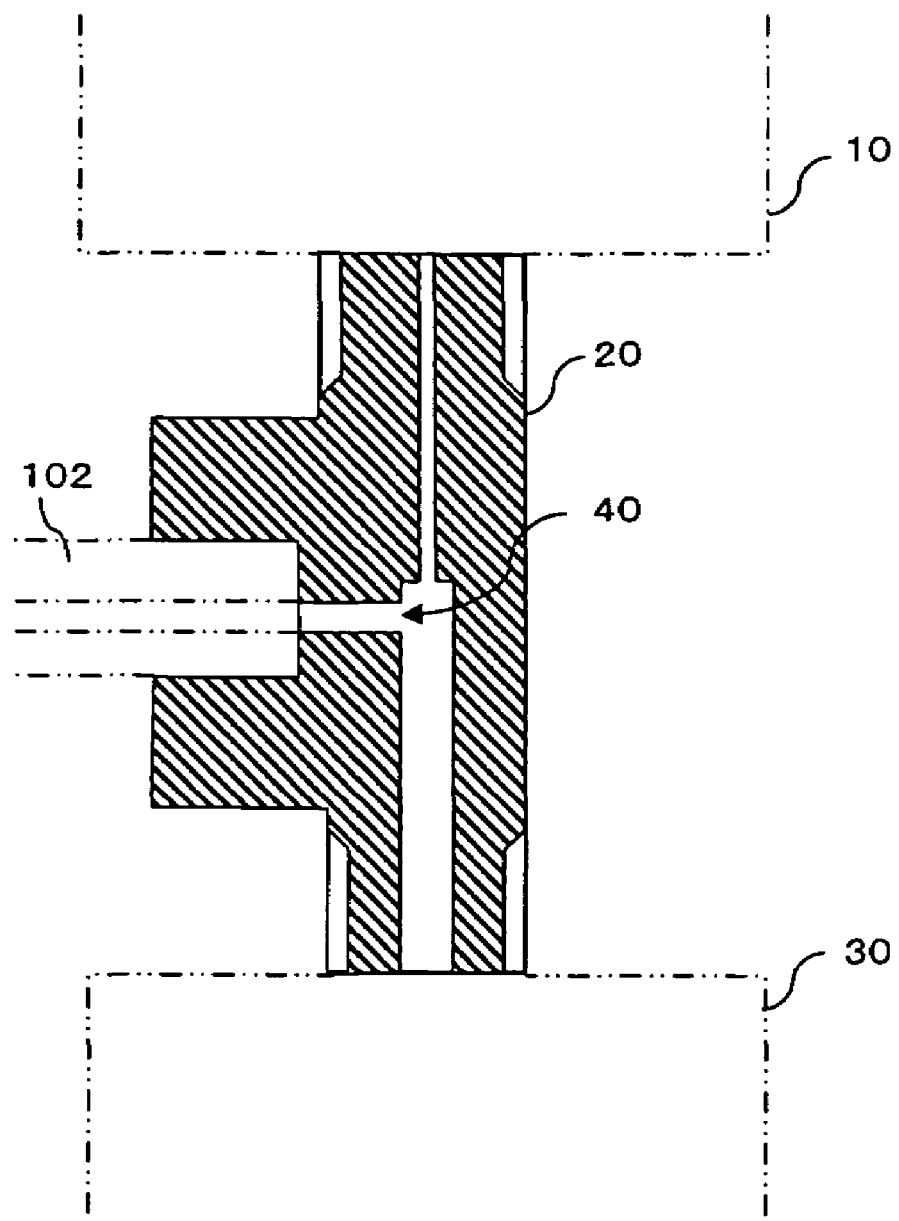
FIG. 14 shows a sectional view of a structure of a branch node.

The inside structure of the straight pipe 20 used in the first embodiment is illustrated in FIG. 14.

The straight pipe 20 is configured so that its inner diameter downward from the branch node 40 to the adsorbing column be larger than the inner diameter upward from the branch node 40 to the reservoir 10. According to this structure, a resistance of the eluant to a direction to the reservoir 10 becomes larger at feeding the eluant in the recovery process. In result, the eluant is hard to run backward to the reservoir 10, in cooperation with the effect that the 2-way valve 110 is closed.

The adsorbing column 30 is filled with the adsorbing material S3 as described above, with the result that the flow of the solvent injected in the reservoir 10 could get worse in the adsorbing column 30 when in the solvent supply process (Step S403). There is a possibility that the solvent does not run in the solvent discharge pipe 105 through the adsorbing column 30, but discharged in the recovery pipe 102.

Figure 12:
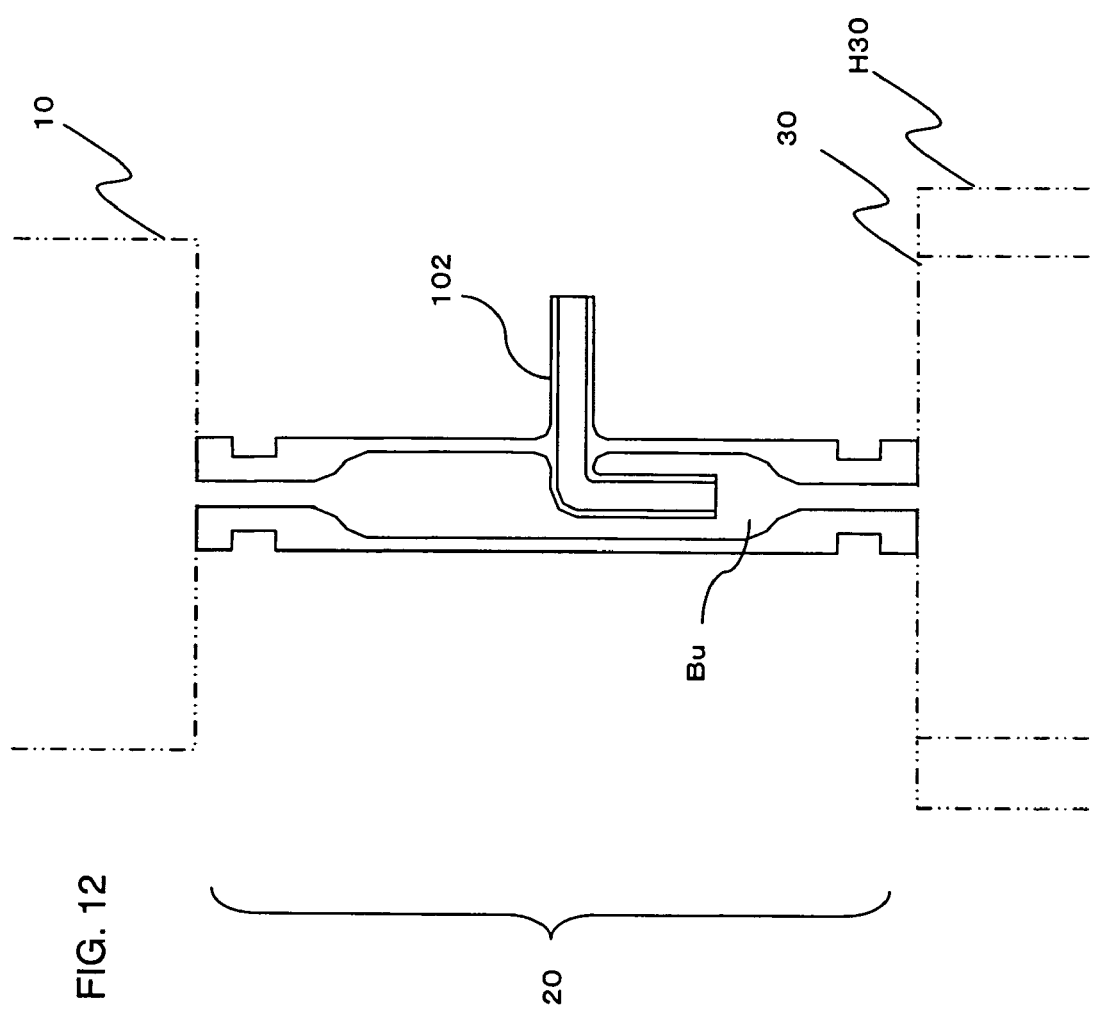
FIG. 12 shows a sectional view of a buffer.

Then, the straight pipe 20 is provided with a buffer Bu by thickening a part of the inner diameter around the branch node diverting to the recovery pipe 102, as shown in FIG. 12. Since the straight pipe 20 is provided with the buffer Bu, even when the flow of the solvent to the adsorbing column 30 gets worse in the solvent supply process, the solvent stays at the buffer Bu. Accordingly, it is possible to avoid that the solvent runs out in the recovery pipe 102.

In addition, in order to make it easy to run in the recovery pipe 102 the eluant in which the dioxin adsorbed to the adsorbing column 30 is dissolved, the end of the recovery pipe 102 may be configured as shown in FIG. 12. That is to say, the end of the recovery pipe 102 may be projected to a position near to the bottom of the buffer Bu and may open toward the adsorbing column 30.

Embodiment 3

Figure 13A:
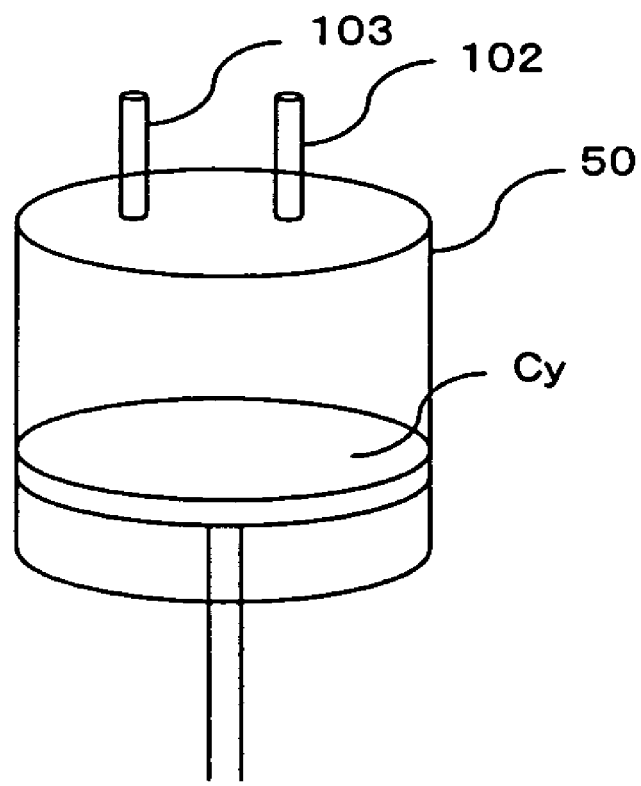
FIG. 13 shows a recovery vessel provided with a syringe.
Figure 13B:
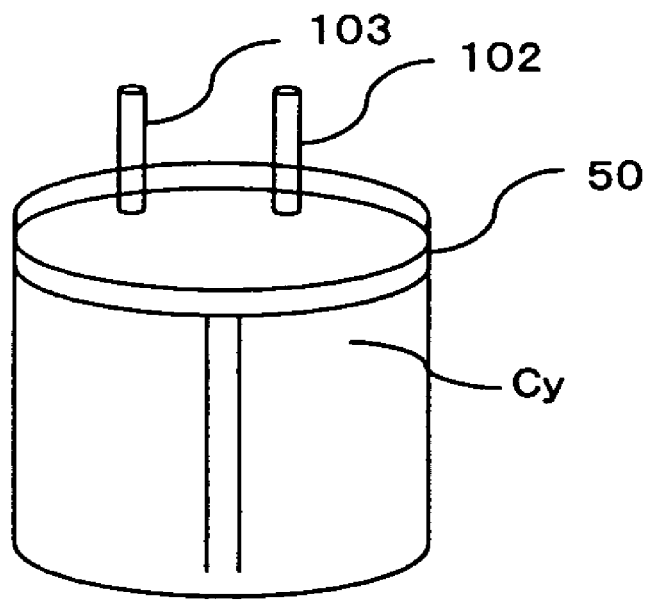

In order to absolutely avoid running the solvent in the recovery pipe 102 at injecting it in the solvent supply process (Step S403), the 3-way valve 130 could block the discharge pipe 103 and the vent pipe 108, and a syringe Cy could be provided in the recovery vessel 50 as shown in FIG. 13A. When the solvent runs down, the volume of the recovery vessel 50 may be 0 by the syringe Cy.

Where the device in the first embodiment has the recovery vessel 50 with the syringe Cy, the solvent supply control unit 310 raises the syringe Cy upwards immediately before the feeding of the solvent as shown in FIG. 13B, and blocks off the end of the recovery pipe 102.

The drying control unit 330 turns back the syringe Cy as shown in FIG. 13A immediately before the feeding of the nitrogen (Step S405) so as to pump the nitrogen in the adsorbing column 30 in the drying process, and opens the recovery pipe 102 and the discharge pipe 103 toward the recovery vessel 50.

If there is no drying process of drying the adsorbing column 30 by the nitrogen, in stead of the drying control unit 330, the recovery control unit 320 turns back the syringe to the state as shown in FIG. 13A immediately before the feeding of the eluant, and then opens the recovery pipe 102 and the discharge pipe 103 toward the recovery vessel 50.

Embodiment 4

Though it is defined in the above-mentioned embodiments that the first valve is the 2-way valve, the second valve is the 3-way valve, and the third valve is the 3-way valve, the invention is not limited to this. Where the activated carbon is used as the adsorbing material, the dioxin and PCB (Polychlorinated Biphenyl) are adsorbed to the adsorbing material.

In order to recover the dioxin separated from PCB, after recovering PCB by using a mixed liquid of dichloromethane and hexane as the eluant, the dioxin is recovered by using the toluene.

Figure 15:
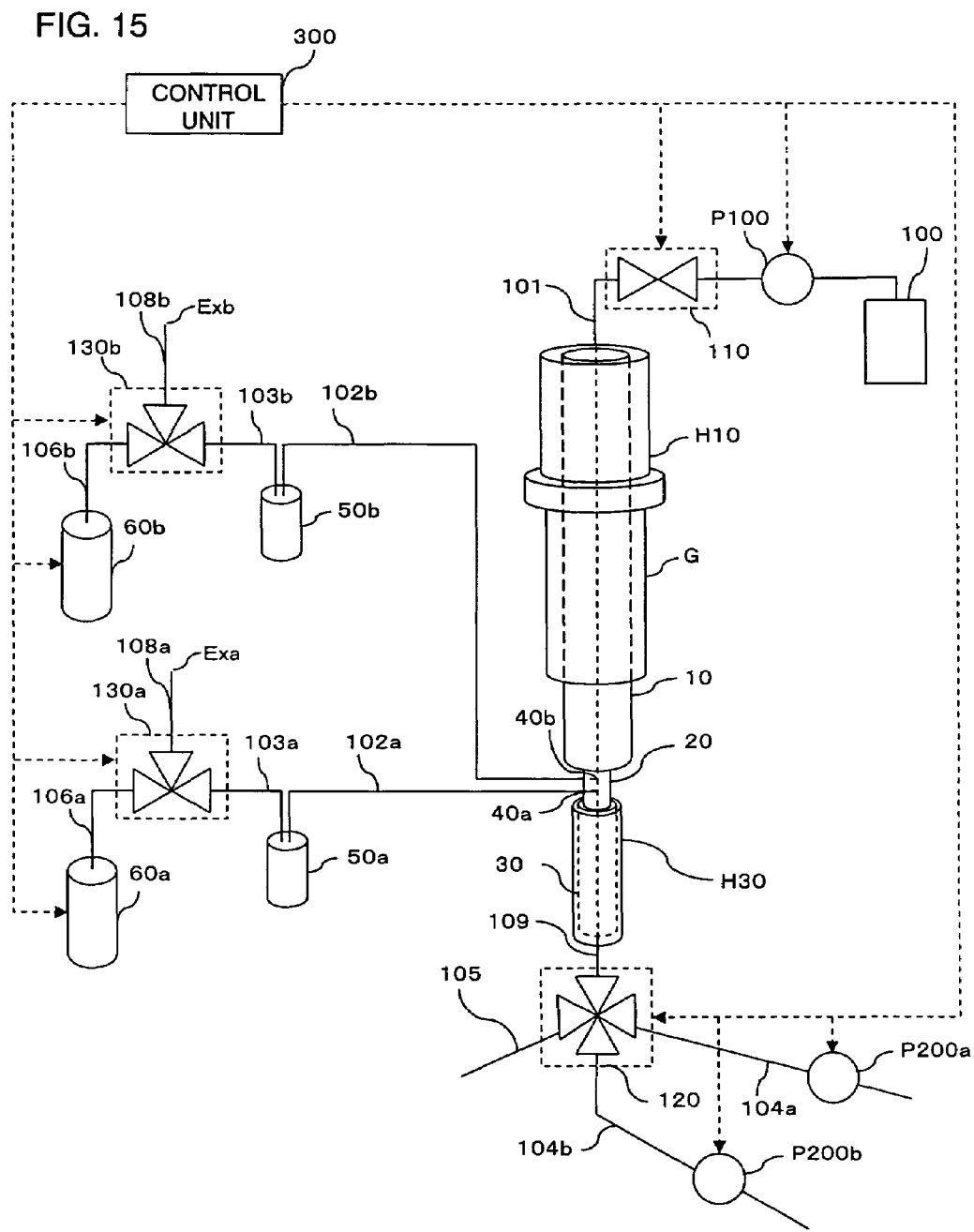
FIG. 15 shows a conceptual diagram illustrating another structure of the present invention.

The process can be executed by a configuration as shown in FIG. 15; the second valve is a 4-way valve, one end of the valve is connected to the common pipe 109 in the same way as above, another end is connected to the solvent discharge pipe 105, and one of the residual two ends is connected to an eluant supply pipe 104a for supplying the mixed liquid of the dichloromethane and hexane and a plump P200a, the other end is connected to an eluant supply pipe 104b for supplying the toluene and a plump P200b. According to such configuration, it is possible to recover more kinds of material automatically.

Moreover, in case of the above configuration, the recovery vessel 50 must be changed at recovering the PCB and at recovering the dioxin, however, such inconvenience can be settled by including two and more branch nodes 40 of the straight pipe 20. Specifically, an attachment structure of the recovery pipe 102a (102b), the recovery vessel 50a (50b), and the third valve 130a (130b), those being disposed on the downstream of the branch node 40, may have the same for every system, and only the recovery vessel 50a (50b) corresponding to the material to be measured may be configured to open via the vent pipe 108a or 108b. In result, there is no need to change the recovery pipe whenever the material to be recovered is different, as mentioned above.

In addition, the heating control is performed on the reservoir 10 in the solvent supply process, but this control is not always required. The heating control in the drying process and the recovery process is not always required, too. Each member (the supply pipe 101 to 109, the straight pipe 20, valves 110, 120 and 130) can use fluorocarbon resin such as polytetrafluoroethylene.

INDUSTRIAL APPLICABILITY

In the device for recovering the material to be measured and the method for recovering the material to be measured in the invention, the material to be measured does not pass through any valve after the sample is impregnated to the sample holding material filled in the reservoir till the sample liquid is recovered in the recovery vessel, so that it is possible to realize the high recovery percentage of the material to be measured. In addition, the invention does not require cleaning the valves whenever the recovery operation is performed, and there is no secondary contamination, so that the invention is useful for the device for recovering the material to be measured and the method for recovering the material to be measured.

The invention claimed is:

1. A device for recovering a material to be measured for dissolving the material in a solvent held by a reservoir to impregnate the solvent to an adsorbing column, eluting the adsorbed material with an eluant, and recovering the material in a recovery vessel, the device comprising:
   a straight pipe communicating an out-flow side of the reservoir with an in-flow side of the adsorbing column; and
   a branch node, branching at a middle of the straight pipe, connectable to a recovery pipe communicated with the recovery vessel
   a first valve configured to open and close an in-flow side of the reservoir to feed the solvent therein for dissolving the material to be measured;
   a second valve on an out-flow side of the adsorbing column configured to switch between a discharge of the solvent and a supply of the eluant for recovering the material to be measured adsorbed in the adsorbing column;

the recovery vessel being provided to the recovery pipe;

a vent hole being communicated with the recovery vessel; and a third valve configure to open and close the vent hole.

2. A device for recovering a material to be measured according to claim 1, wherein the reservoir is filled with a filter material to preparatively purify a sample liquid in which the material to be measured is dissolved.

3. A device for recovering a material to be measured according to claim 1, wherein a lower part of the straight pipe including the branch node is thicker in inner diameter than an upper part of the straight pipe.

4. A device for recovering a material to be measured according to claim 1, wherein the branch node of the straight pipe is provided with a buffer by thickening a part of the inner diameter around the branch node than the other part, and the recovery pipe is projected to inside of the straight pipe and opens toward the adsorbing column.

5. A device for recovering a material to be measured according to claim 1, wherein the second valve enables to selectively alternate plural eluants.

6. A device for recovering a material to be measured according to claim 3, wherein the straight pipe is provided with one and more branch nodes.

7. A device for recovering a material to be measured according to claim 1, wherein the recovery vessel is provided with a syringe to vary the volume thereof.

8. A device for recovering a material to be measured according to claim 1, the device comprising:

a gas vessel filled with a gas to dry the adsorbing column;

a gas supply pipe configured to supply the gas to the adsorbing column; and the third valve configured to communicate or block off between the gas supply pipe and the recovery vessel.

9. A device for recovering a material to be measured according to claim 1, the device comprising:

a solvent supply control unit configured to open the first valve, turn the second valve to discharge the solvent, and close the vent hole by the third valve, at feeding the solvent in the reservoir; and a recovery control unit configured to close the first valve, turn the second valve to supply the eluant, and open the vent hole by the third valve, at eluting the material to be measured absorbed in the adsorbing column.

10. A device for recovering a material to be measured according to claim 1, comprising a drying control unit configured to dry a path of the eluant after the solvent supply control unit ran the eluant therein.

11. A device for recovering a material to be measured according to claim 1, comprising a discharge control unit configured to discharge the residual eluant after the solvent supply control unit ran the eluant therein.

12. A method for recovering a material to be measured, comprising:

opening an in-flow side of a reservoir holding the material to be measured, communicating an out-flow side of an adsorbing column adsorbing the material with a solvent discharge pipe discharging a solvent, and closing a vent hole communicated with a recovery vessel provided to a recovery pipe branched from a straight pipe communicating the reservoir and the adsorbing column;

feeding the solvent from the in-flow side of the reservoir;

closing the in-flow side of the reservoir, communicating the out-flow side of the adsorbing column with the eluant supply pipe supplying the eluant for recovering the material adsorbed in the adsorbing column, and opening the vent hole; and feeding the eluant from the eluant supply pipe to the adsorbing column.

* * * * *